US008862195B2

(12) United States Patent
Hornero Sanchez et al.

(10) Patent No.: US 8,862,195 B2
(45) Date of Patent: Oct. 14, 2014

(54) METHOD, SYSTEM, AND APPARATUS FOR AUTOMATIC DETECTION OF OBSTRUCTIVE SLEEP APNEA FROM OXYGEN SATURATION RECORDINGS

(75) Inventors: Roberto Hornero Sanchez, Valladolid (ES); Jose Victor Marcos Martin, Valladolid (ES); Daniel Alvarez Gonzalez, Valladolid (ES); Pedro Mateo Riobo Aboy, Beaverton, OR (US); Felix Del Campo Matias, Valladolid (ES)

(73) Assignee: University of Valladolid, Valladolid (ES)

( * ) Notice: Subject to any disclaimer, the term of this patent is extended or adjusted under 35 U.S.C. 154(b) by 696 days.

(21) Appl. No.: 13/044,846

(22) Filed: Mar. 10, 2011

(65) Prior Publication Data
US 2011/0224517 A1 Sep. 15, 2011

Related U.S. Application Data

(60) Provisional application No. 61/312,252, filed on Mar. 10, 2010.

(51) Int. Cl.
*A61B 5/1455* (2006.01)
*A61B 5/00* (2006.01)

(52) U.S. Cl.
CPC ............ *A61B 5/4818* (2013.01); *A61B 5/7264* (2013.01); *A61B 5/14551* (2013.01)
USPC .......................................... 600/323; 600/310

(58) Field of Classification Search
USPC ......... 600/300, 301, 310, 322, 323, 324, 473, 600/476; 356/41; 702/66, 75, 76, 77
See application file for complete search history.

(56) References Cited

U.S. PATENT DOCUMENTS

| | | | |
|---|---|---|---|
| 6,405,065 B1 * | 6/2002 | Malin et al. | 600/310 |
| 6,748,252 B2 * | 6/2004 | Lynn et al. | 600/323 |
| 7,309,314 B2 | 12/2007 | Grant et al. | |
| 7,785,262 B2 | 8/2010 | Melker et al. | |
| 2005/0131283 A1 | 6/2005 | Grant et al. | |
| 2006/0241506 A1 | 10/2006 | Melker et al. | |

OTHER PUBLICATIONS

Alvarez et al., "Nonlinear characteristics of blood oxygen saturation from nocturnal oximetry for obstructive sleep apnoea detection", Physiol. Meas. 27 (2006) 399-412.*
Marcos et al., "Assessment of four statistical pattern recognition techniques to assist in obstructive sleep apnoea diagnosis from nocturnal oximetry", Medical Engineering & Physics 31 (2009) 971-978.*
J.Victor Marcos, et al. Automated detection of obstructive sleep apnoea syndrome from oxygen saturation recordings using linear discriminant analysis. Medical & Biological Engineering Computing (Jun. 24, 2010) 48:895-902.

* cited by examiner

*Primary Examiner* — Tse Chen
*Assistant Examiner* — Chu Chuan (JJ) Liu
(74) *Attorney, Agent, or Firm* — Mateo Aboy; Aboy & Associates PC

(57) ABSTRACT

Disclosed embodiments include a method for automatic detection of sleep apnea implemented in a medical apparatus, the method comprising (a) extracting a plurality of signal features by analyzing an oxygen saturation signal, (b) performing dimensionality reduction on the plurality of signal features to generate a plurality of signal features in a transformed space; and (c) displaying a sleep apnea diagnosis result based on a statistical classifier that operates on the plurality of signal features in a transformed space.

5 Claims, 5 Drawing Sheets

METHOD, SYSTEM, AND APPARATUS FOR AUTOMATIC DETECTION OF OBSTRUCTIVE SLEEP APNEA FROM OXYGEN SATURATION RECORDINGS

CROSS-REFERENCE TO RELATED APPLICATIONS

This application also claims the benefit of U.S. Provisional Application No. 61/312,252 filed on 2010-03-10, which is incorporated herein by reference in its entirety.

TECHNICAL FIELD

This invention relates to methods, systems, and apparatus for sleep apnea monitoring. Specifically, it relates to methods, systems, and apparatus for non-invasive detection of obstructive sleep apnea from oxygen saturation.

BACKGROUND

Obstructive sleep apnea syndrome (OSAS) is the most common form of sleep disordered-breathing. Epidemiological studies estimate its prevalence up to 5% of adult men in western countries. OSAS is characterized by repetitive occlusion of the upper airway during sleep, causing intermittent cessations of breathing (apneas) or reduction in airflow (hypopneas). Events of apnea are accompanied by hypoxemia and bradycardia. They are often terminated in arousals, and the resulting sleep fragmentation can lead to excessive daytime sleepiness. As a result, OSAS has been pointed out as a major cause of traffic and industrial accidents. Additionally, long-term effects are related to the cardiovascular system, including hypertension, arrhythmias, congestive heart failure and cerebrovascular disease. A high percentage of patients, 83% of men and 93% of women, remains undiagnosed. Therefore, OSAS can be considered as a risk factor for public health.

Nowadays, nocturnal polysomnography (PSG) is considered the gold-standard for OSAS diagnosis. It must be performed in a special sleep unit and under supervision of a trained technician. PSG monitors different physiological recordings such as electrocardiogram (ECG), electroencephalogram (EEG), electrooculogram (EOG), electromyogram (EMG), oxygen saturation, abdominal ventilatory effort and snoring. These recordings must be subsequently analyzed by a medical expert to obtain a final diagnosis. Despite its high diagnostic performance, PSG presents some drawbacks since it is complex, expensive and time-consuming. As a result, the research focused on the development of alternative diagnostic techniques has notably increased in recent years, such us the use of medical systems based on nocturnal pulse oximetry.

Nocturnal pulse oximetry allows to monitor respiratory dynamics during sleep by measuring arterial oxygen saturation (SaO2). This recording provides useful information about OSAS. Events of apnea are characterized by a decrease in the SaO2 value, which reflects airflow reduction and hypoxemia. Subsequently, respiration is restored and the saturation value increases until its baseline level. As a result, SaO2 signals from OSAS patients tend to be more unstable than those from control subjects due to the recurrence of apneas during sleep. This different behavior can be exploited to diagnose OSAS. Diverse methodologies have been proposed to perform OSAS diagnosis from SaO2 data. The simplest one is visual inspection. However, it is tedious and subjective. Therefore, automated analysis of SaO2 data would be desirable. Conventional oximetry indices represent a first approach for this purpose. These indices are the oxygen desaturation index over 2% (ODI2), 3% (ODI3) and 4% (ODI4), and the cumulative time spent below 90% of saturation (CT90). However, improved OSAS diagnosis from SaO2 recordings is possible by using more advanced computer-implemented signal processing methods.

Related art includes U.S. patent application Ser. No. 10/947,983 which discloses a method for diagnosing OSAS based on a tool for the predicting Apnea Hypopnea Index (AHI) using non-parametric analysis and bootstrap aggregation; U.S. patent application Ser. No. 11/122,278 which discloses a method for monitoring respiration involving processing plethysmography signals; and U.S. patent application Ser. No. 10/30/2008 which discloses a computer-implemented method for patient monitoring based on processing signals to detect breathing patterns. Disadvantageously, none of the related art provides a complete method or system that enables for automatic detection of OSAS based on pulse oximetry with classification accuracies appropriate for clinical use.

SUMMARY

Disclosed embodiments, without limitation, include a method for automatic detection of sleep apnea implemented in a medical apparatus including an oxygen saturation signal acquisition circuit, one or more processors, one or more memories, and one or more displays; the method comprising: (a) extracting a plurality of signal features by analyzing an oxygen saturation signal acquired by the signal acquisition hardware; (b) performing dimensionality reduction on the plurality of signal features to generate a plurality of signal features in a transformed space; and (c) displaying a sleep apnea diagnosis result on the displays of the medical apparatus based on a statistical classifier that operates on the plurality of signal features in a transformed space. According to a particular embodiment and without limitation, the signal features include a plurality of spectral metrics based on power spectral density and a plurality of nonlinear metrics including Approximate Entropy, Central Tendency Measure, and Lempel-Ziv complexity. The dimensionality reduction is performed by a method substantially equivalent to principal component analysis, and the statistical classifier is substantially equivalent to linear discriminant analysis. Alternative embodiments may employ other statistical classifiers including quadratic discriminant analysis, k-nearest neighbors, and logistic regression.

BRIEF DESCRIPTION OF THE DRAWINGS

Disclosed embodiments are illustrated by way of example, and not by way of limitation, in the figures of the accompanying drawings.

DETAILED DESCRIPTION

Figure 1:
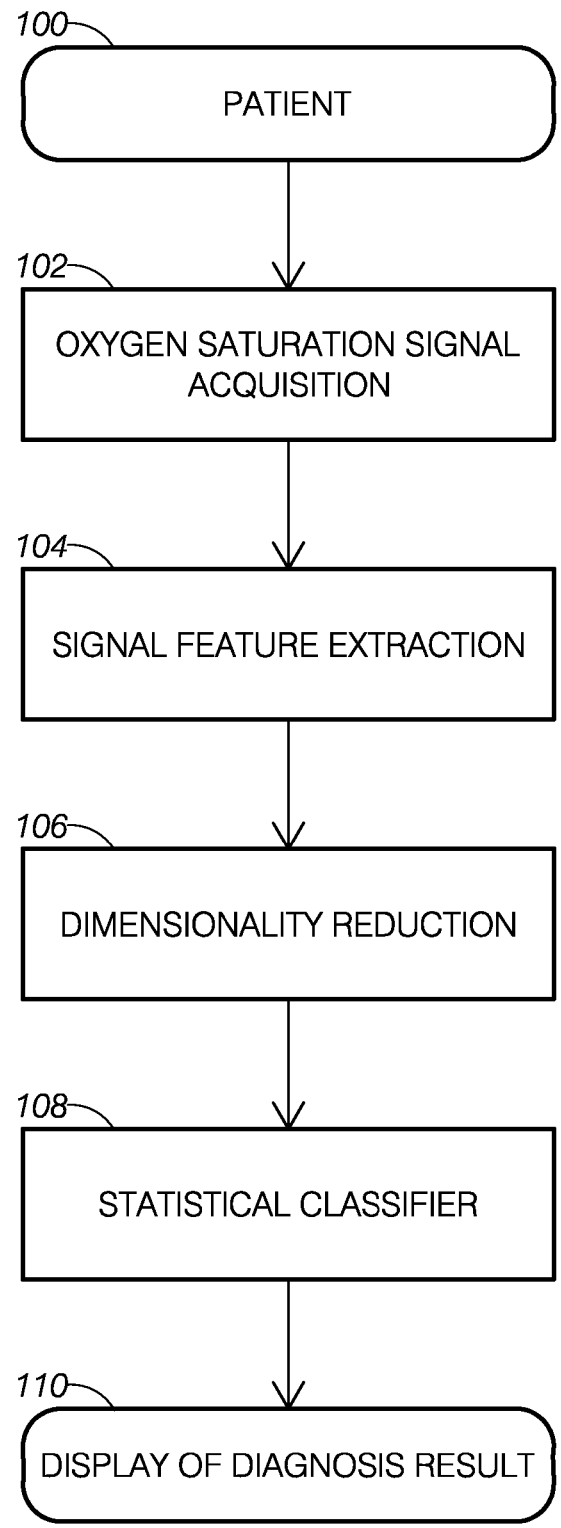
FIG. 1 shows a block diagram of the method according to one embodiment.

FIG. 1 shows a block diagram of the method according to one embodiment. Disclosed embodiments include a method for automatic detection of sleep apnea implemented in a medical apparatus including an oxygen saturation signal acquisition circuit 102, one or more processors, one or more memories, and one or more displays; the method comprising: (a) extracting a plurality of signal features by analyzing an oxygen saturation signal acquired by the signal acquisition hardware 104; (b) performing dimensionality reduction on the plurality of signal features to generate a plurality of signal features in a transformed space 106; and (c) displaying a sleep apnea diagnosis result 110 on the displays of the medical apparatus based on a statistical classifier 108 that operates on the plurality of signal features in a transformed space.

Figure 2:
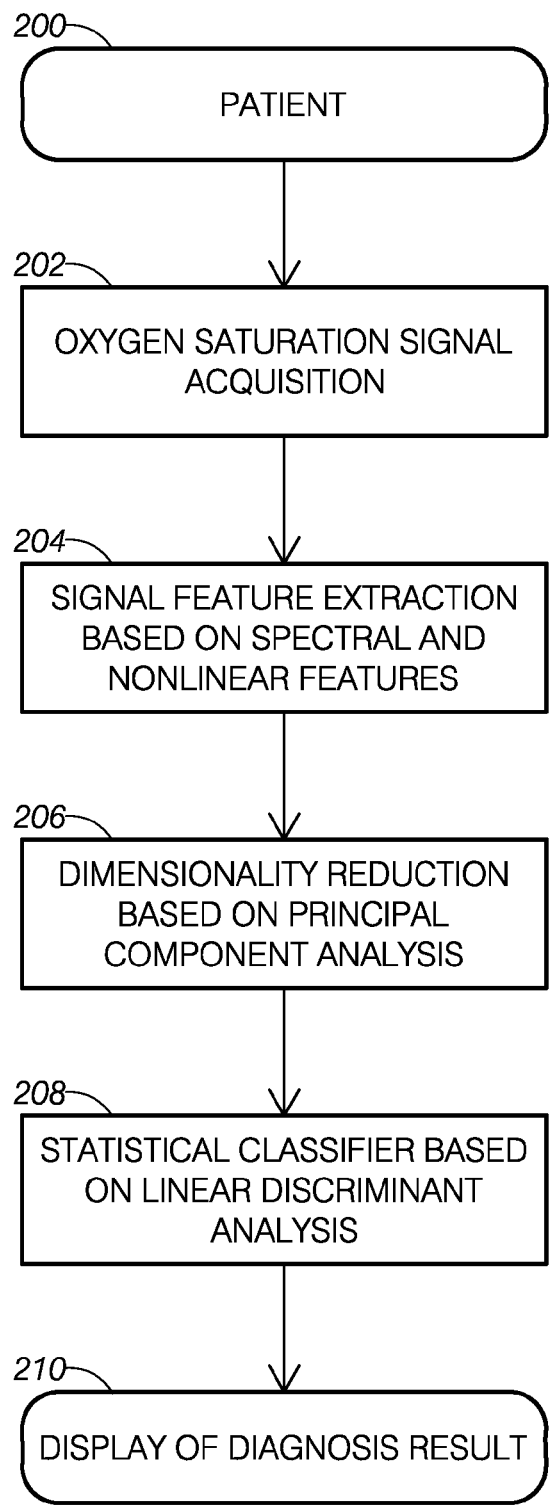
FIG. 2 shows a block diagram of the method according to a particular embodiment.

FIG. 2 shows a block diagram of the method according to a particular embodiment. According to this particular embodiment, and without limitation, the signal features include a plurality of spectral metrics based on power spectral density and a plurality of nonlinear metrics 204 including Approximate Entropy, Central Tendency Measure, and Lempel-Ziv complexity. The dimensionality reduction is performed by a method substantially equivalent to principal component analysis 206 and the statistical classifier is substantially equivalent to linear discriminant analysis 208. Alternative embodiments may employ other statistical classifiers including quadratic discriminant analysis, k-nearest neighbors, and logistic regression.

According to a specific embodiment, the method can be implemented in a medical system with one or more processors, physiological signal acquisition, analog-to-digital and digital-to-analog converters, one or more memories, and one or more output displays such as the typical bedside monitors used in clinical settings. Alternatively, it can be implemented in a digital computer with one or more processors to analyze physiological signals and display the results, output the results in the form of a printed or electronic clinical report, or send the results over a network to a receiving node for further clinical analysis and use. Consequently, in this disclosure we present a method for automatic detection or diagnosis of sleep apnea. Such method can be implemented in a stand-alone medical apparatus such as a bedside monitor with the hardware elements disclosed above. Alternatively, it may be implemented as a system that includes a plurality of methods, apparatuses, and a networks infrastructure.

A. Detailed Method Description

Figure 3:
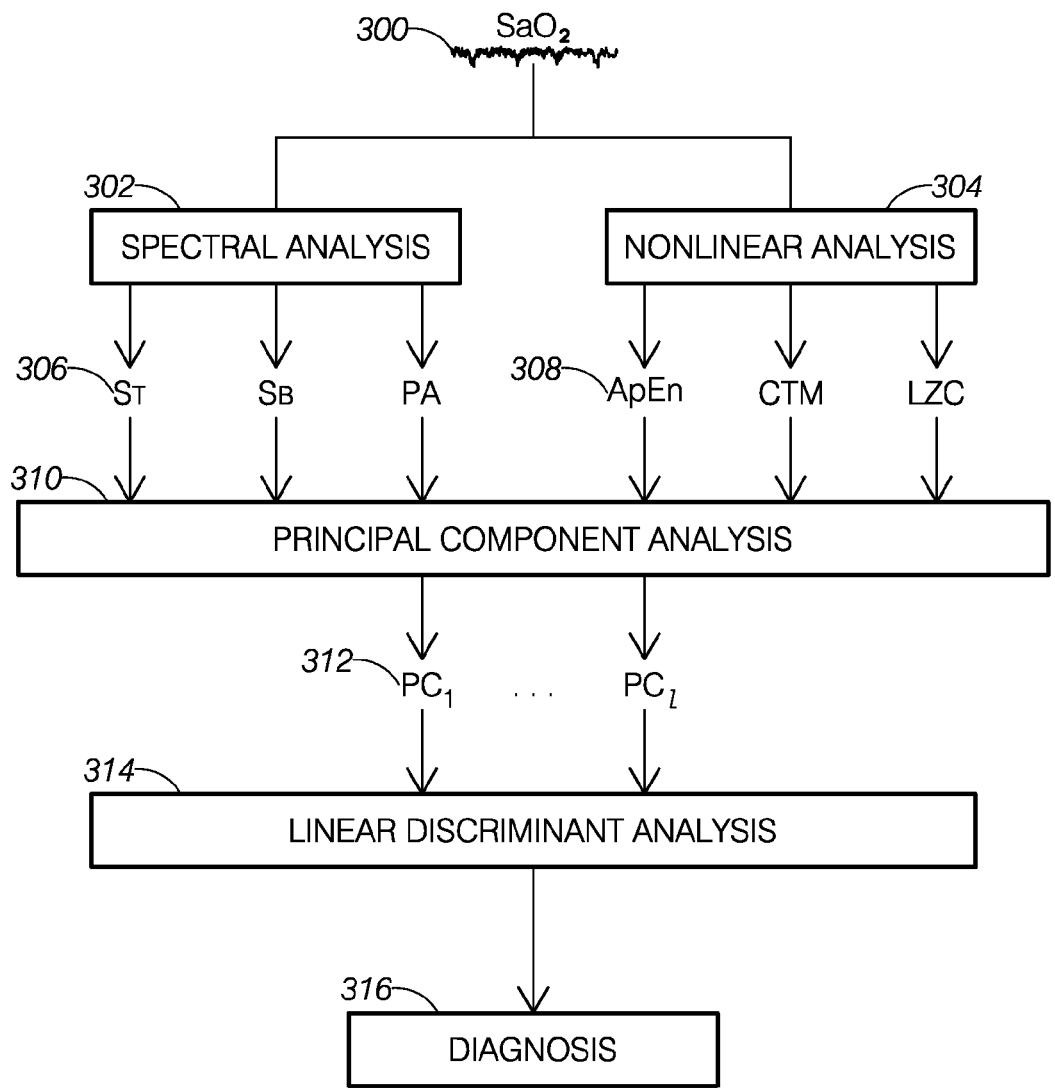
FIG. 3 shows a block diagram of the method according to a particular embodiment.

FIG. 3 shows a block diagram of the method according to a particular embodiment including additional implementation details. The following sections describe a detailed description of the method according to one particular embodiment disclosed herein to illustrate one possible reduction to practice by way of example. While particular embodiments are described, it is understood that, after learning the teachings contained in this disclosure, modifications and generalizations will be apparent to those skilled in the art without departing from the spirit of the disclosed embodiments.

A.1. Step 1—Feature Extraction

The feature extraction stage maps the SaO2 signal 300 into a reduced set of variables or features to summarize the information in the recording. The extracted features measure relevant properties of oximetry data in order to discriminate signals from OSAS positive subjects. Spectral 302 and nonlinear 304 analyses of SaO2 signals 300 provide valuable information to detect OSAS. Statistically significant differences were found between OSAS positive and negative subjects by evaluating different spectral and nonlinear features. Consequently, according to one embodiment our proposed automatic OSAS detection method uses both spectral analysis and nonlinear analysis for feature extraction.

A.1.1. Spectral Analysis

Periodicities of ventilation originate phase-lagged changes in SaO2 data 300. The duration of apnea events ranges from 30 s to 2 min, including the awakening response after the event. These events are reflected in oximetry recordings by a fluctuation (decrease and subsequent restoration of the saturation value) with the same duration. The recurrence of apneas during sleep infers some periodic behavior in SaO2 signals 300. Due to the duration of the events, the repetition of changes in these signals occurs with a rate between 30 s and 2 min. The frequency band associated to these periods of fluctuation ranges between 0.010 and 0.033 Hz. Thus, the signal power contained in this band is usually higher in subjects with OSAS than in controls.

According to a particular embodiment, and without limitation, the proposed OSAS detection method calculates the following spectral features 306 computed from the power spectral density (PSD) 302 of SaO2 data 300:

Feature 1. Total area under the PSD ($S_T$). This feature provides an estimate of the signal power.

Feature 2. Area enclosed in the band of interest ($S_B$). This feature approximates the amount of signal power contained in the band between 0.010 and 0.033 Hz.

Feature 3. Peak amplitude of the PSD in the band of interest ($P_A$). It represents the most significant frequency component contained in the band between 0.010 and 0.033 Hz.

According to the dynamical behavior of SaO2 recordings 300, these spectral features 306 are expected to be higher in signals corresponding to OSAS positive subjects. However, alternative frequency ranges can be used with correlated results.

A.1.2. Nonlinear Analysis

SaO2 signals 300 from patients affected by OSAS tend to present frequent changes and fluctuations due to the repetition of apneas. In contrast, oximetry recordings corresponding to control subjects tend to have a near-constant value of saturation around 97%. Nonlinear analysis 304 of oximetry data can capture these differences, representing a useful means to quantitatively distinguish OSAS patients from control subjects. According to a particular embodiment, and without limitation, the proposed OSAS detection method calculates the following nonlinear metrics 308 from the SaO2 recordings during the feature extraction stage:

Feature 4. Approximate entropy (ApEn). It provides an estimate of the irregularity of a signal. High values of ApEn correspond to irregular signals. Two input parameters must be specified to compute ApEn: a run length m and a tolerance window r. Briefly, ApEn measures the logarithmic likelihood that runs of patterns that are close (within r) for m contiguous observations remain close (within the same tolerance width r) on subsequent incremental comparisons.

Feature 5. Central tendency measure (CTM). It quantifies the variability of a time series, assigning low values to signals with a high degree of chaos. Second-order difference plots are generated by plotting $(s_{t+2}-s_{t+j})$ vs. $(s_{t+1}-s_t)$, where $s_t$ is the time series of length T. Then, CTM is computed by selecting a circular region of radius r round the origin, counting the number of points that fall within the radius and dividing by the total number of points.

Feature 6. Lempel-Ziv complexity (LZC). It is a non-parametric, simple-to-calculate measure of complexity in a one-dimensional signal. Complex signals generate high values of LZC. This feature is related to the number of distinct substrings and the rate of their recurrence along a given sequence. The signal must be transformed into a finite symbol sequence before calculating the complexity measure. The transformation is carried out by comparing each sample with a fixed threshold. Usually, the median value is used to obtain a 0-1 sequence. Then, this binary sequence is scanned from left to right and the complexity counter is increased by one unit every time a new subsequence of consecutive characters is encountered.

The presence of OSAS is related to irregularity, variability and complexity of SaO2 measured by ApEn, CTM and LZC 308, respectively. As a result, high values of ApEn and LZC as well as low CTM values are expected for recordings from OSAS positive subjects.

A.2. Step 2—Preprocessing: Principal Component Analysis (PCA)

According to a particular embodiment, once the method obtains the spectral ($S_T$, $S_B$, PA) 306 and nonlinear features (ApEn, CTM, LZC) 308 during the feature extraction stage, it performs PCA 310 before the pattern classification stage 314. PCA is usually applied to perform dimensionality reduction. Vectors x in a d-dimensional space are mapped into a l-dimensional space, where l≤d is determined according to a given criterion. Samples of variable x in the original space are defined by the spectral and nonlinear features from SaO2 recordings (d=6). PCA produces an uncorrelated set of d variables or components by projecting the input data onto the eigenvectors of the covariance matrix of variable x. These eigenvectors constitute an orthonormal basis in the original space. Additionally, the new d components are ranked by PCA in decreasing importance since the amount of variance along a particular eigenvector is represented by its associated eigenvalue. In this embodiment the method proceeds as follows:

1. The mean of the vectors in the original space is computed and subtracted.
2. The covariance matrix is calculated and its eigenvectors and eigenvalues are found.
3. The eigenvectors corresponding to the l largest eigenvalues are retained.
4. The original vectors are projected onto the eigenvectors to give the components of the transformed vectors in the l-dimensional space.

Each component obtained from PCA is a linear combination of features in the original space and the first l components are selected to define the dimension of the transformed space.

A.3. Step 3—Classification: Linear Discriminant Analysis (LDA)

In this step, the variables selected 312 from PCA 310 are the inputs to the statistical classifier based on LDA 314. Classifiers based on LDA makes two prior hypotheses about the statistical distribution of the input variables. First, the distributions of samples in both classes are required to be normal. Additionally, it is supposed that all the class covariance matrices are identical (homocedasticity). Applying PCA to the spectral and nonlinear parameters results in input variables that better satisfy the statistical requirements of LDA. Alternative embodiments may employ other statistical classifiers including quadratic discriminant analysis, k-nearest neighbors, and logistic regression.

While particular embodiments have been described, it is understood that, after learning the teachings contained in this disclosure, modifications and generalizations will be apparent to those skilled in the art without departing from the spirit of the disclosed embodiments.

B. Example Performance Results

Figure 4:
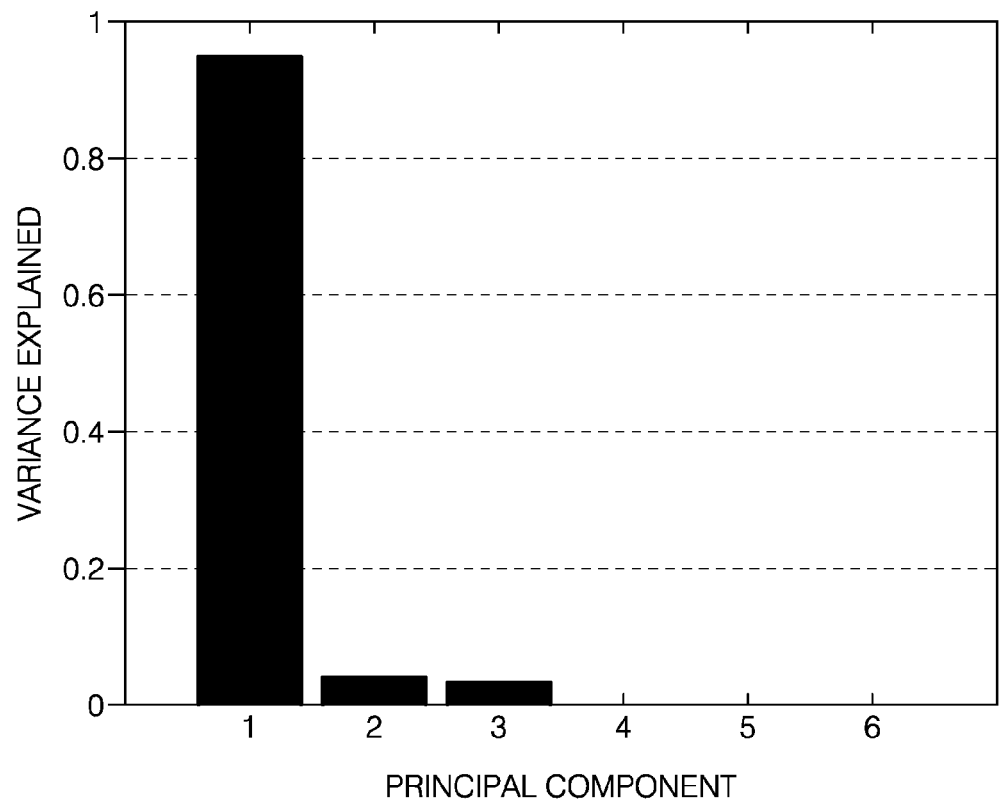
FIG. 4 shows the results of a study to determine the variance explained by the principal components.

A validation study was conducted to evaluate the performance of a particular embodiment of the OSA detection method, system, and apparatus. The results of this assessment study to evaluate a particular embodiment of the computer-implemented method described herein have been reported in the peer-reviewed article entitled "Automated detection of obstructive sleep apnoea syndrome from oxygen saturation recordings using linear discriminant analysis" published in Med Biol Eng Comput. 2010 September; 48(9):895-902 which is hereby incorporated herein by reference in its entirety. Specifically, a scientific study was conducted to characterize and prospectively validate a particular embodiment of the proposed OSAS detection algorithm. The population under study was composed of subjects suspected of suffering from OSAS. A total of 214 SaO2 signals were used. These signals were randomly divided into a training set (85 signals) and a test set (129 signals) to prospectively validate the proposed method and system. The OSAS detection algorithm achieved a diagnostic accuracy of 93.02% (97.00% sensitivity and 79.31% specificity) on the test set. It outperformed other alternative implementations that either use spectral and nonlinear features separately or are based on logistic regression (LR). The proposed method could be a useful tool to assist in early OSAS diagnosis, contributing to overcome the difficulties of conventional PSG. FIG. 4 shows the results of a study to determine the variance explained by the principal components.

Figure 5:
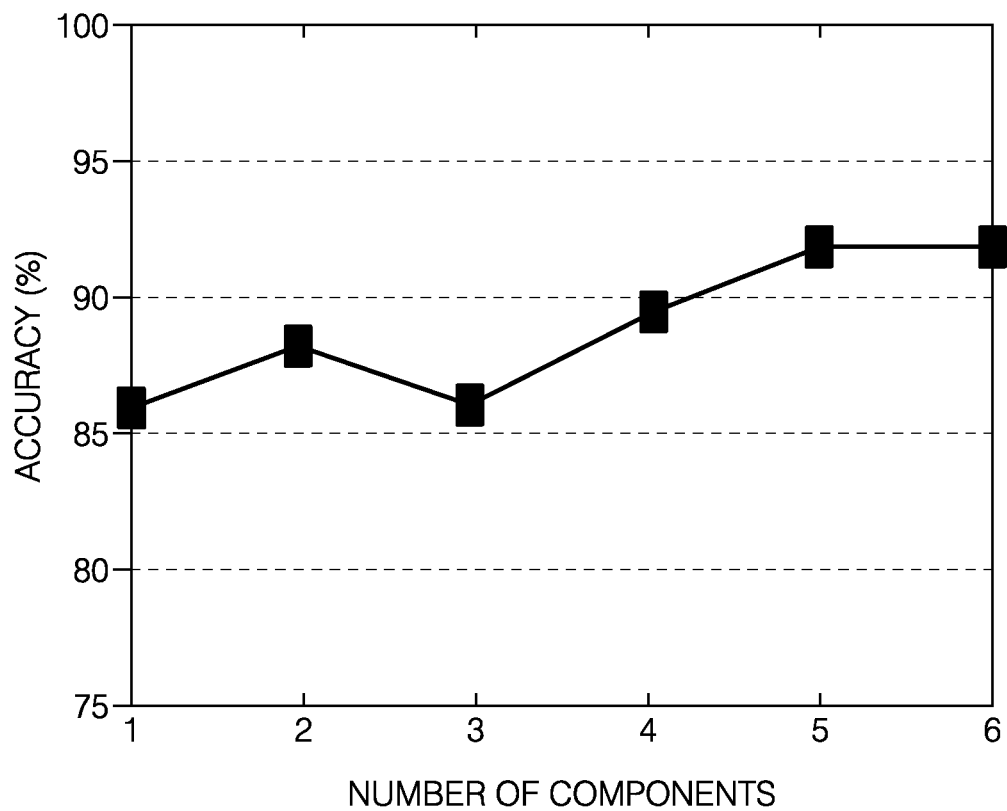
FIG. 5 shows the results of a study to determine the accuracy of a particular embodiment of the method.

FIG. 5 shows the results of a study to determine the accuracy of a particular embodiment of the method.

Certain specific details in the above description and figures to provide a thorough understanding of various embodiments disclosed. Certain well-known details often associated with computing, computer-implemented methods and associated systems, and software technology are not set forth in the following disclosure to avoid unnecessarily obscuring the various disclosed embodiments. Further, those of ordinary skill in the relevant art will understand that they can practice other embodiments without one or more of the details described below. Aspects of the disclosed embodiments may be implemented in the general context of computer-executable instructions, such as program modules, being executed by a computer, computer server, or device containing a processor. Generally, program modules include routines, programs, objects, components, data structures, etc., that perform particular tasks or implement particular abstract data types. Aspects of the disclosed embodiments may also be practiced in distributed computing environments where tasks are performed by remote processing devices that are linked through a communications network. In a distributed computing environment, program modules may be located in both local and remote storage media including memory storage devices. Those skilled in the art will appreciate that given the description of the modules comprising the disclosed embodiments provided in this specification, it is a routine matter to provide working systems that work on a variety of known and commonly available technologies capable of incorporating the features described herein.

While particular embodiments have been described, it is understood that, after learning the teachings contained in this disclosure, modifications and generalizations will be apparent to those skilled in the art without departing from the spirit of the disclosed embodiments. It is noted that the foregoing embodiments and examples have been provided merely for the purpose of explanation and are in no way to be construed as limiting. While the method, system, and/or apparatus has been described with reference to various embodiments, it is understood that the words that have been used herein are words of description and illustration, rather than words of limitation. Further, although the system has been described herein with reference to particular means, materials and embodiments, the actual embodiments are not intended to be limited to the particulars disclosed herein; rather, the system extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosed embodiments in its aspects.

The invention claimed is:

1. A method for automatic detection of sleep apnea implemented in a medical apparatus; said method comprising:
   (a) extracting a plurality of signal features by analyzing an oxygen saturation signal;
   (b) performing dimensionality reduction based on principal component analysis (PCA) on said plurality of signal features to generate a plurality of signal features in a transformed space, wherein said plurality of signal features comprise (1) a plurality of power spectral density metrics including computing a total area under the power spectral density, computing an area over a user-specified frequency band, and computing a peak amplitude over said user-specified frequency band; and (2) a plurality of nonlinear analysis metrics including approximate entropy (ApEn), a central tendency measure (CTM), and Lempel-Ziv complexity (LZC); and (c) reporting a sleep apnea diagnosis result based on a statistical classifier that operates on said plurality of signal features in said transformed space.

2. The method of claim 1, wherein said statistical classifier is based on linear discriminant analysis.

3. The method of claim 1, wherein said statistical classifier is based on a quadratic discriminant analysis.

4. The method of claim 1, wherein said statistical classifier is based on k-nearest neighbors.

5. The method of claim 1, wherein said statistical classifier is based on logistic regression.

* * * * *